(12) United States Patent
Walter et al.

(10) Patent No.: US 9,034,794 B2
(45) Date of Patent: *May 19, 2015

(54) METHOD FOR POST-EMERGENCE CRABGRASS CONTROL

(75) Inventors: James Walter, West Chester, PA (US); Frank Robert Walls, Jr., Goldsboro, NC (US)

(73) Assignee: FMC Corporation, Philadelphia, PA (US)

( * ) Notice: Subject to any disclaimer, the term of this patent is extended or adjusted under 35 U.S.C. 154(b) by 1034 days.

This patent is subject to a terminal disclaimer.

(21) Appl. No.: 12/600,759

(22) PCT Filed: May 29, 2008

(86) PCT No.: PCT/US2008/065107
§ 371 (c)(1),
(2), (4) Date: Nov. 18, 2009

(87) PCT Pub. No.: WO2008/150882
PCT Pub. Date: Dec. 11, 2008

(65) Prior Publication Data
US 2010/0167932 A1    Jul. 1, 2010

Related U.S. Application Data

(60) Provisional application No. 60/932,201, filed on May 30, 2007.

(51) Int. Cl.
*A01N 43/00* (2006.01)
*A01N 33/18* (2006.01)

(52) U.S. Cl.
CPC ..................................... *A01N 33/18* (2013.01)

(58) Field of Classification Search
USPC ........................................................ 504/139
See application file for complete search history.

(56) References Cited

U.S. PATENT DOCUMENTS

| | | |
|---|---|---|
| 3,764,623 A | 10/1973 | Hunter et al. |
| 4,818,275 A | 4/1989 | Theodoridis |
| 5,071,469 A | 12/1991 | Artz |
| 5,510,318 A | 4/1996 | Patel et al. |
| 2004/0235661 A1 | 11/2004 | Mito et al. |

*Primary Examiner* — Alton Pryor
(74) *Attorney, Agent, or Firm* — FMC Corporation

(57) ABSTRACT

The present invention provides a method for post-emergence selective crabgrass control by applying a composition comprising a first herbicide and a second herbicide in which the first herbicide is 2,4-dinitro-$N^3,N^3$-dipropyl-6-(trifluoromethyl)-1,3-benzenediamine and the second herbicide is N-[2,4-dichloro-5-[4-(difluoromethyl)-4,5-dihydro-3-methyl-5-oxo-1H-1,2,4-triazol-1-yl]phenyl]methanesulfonamide to a locus where one to two leaf growth stage crabgrass is present.

5 Claims, No Drawings

METHOD FOR POST-EMERGENCE CRABGRASS CONTROL

This application claims the benefit of U.S. Provisional Application No. 60/932,201 filed May 30, 2007.

FIELD OF THE INVENTION

This invention relates to a method for post-emergence selective crabgrass control in turf sites by applying a composition comprising a first herbicide and a second herbicide in which the first herbicide is 2,4-dinitro-$N^3$,$N^3$-dipropyl-6-(trifluoromethyl)-1,3-benzenediamine and the second herbicide is N-[2,4-dichloro-5-[4-(difluoromethyl)-4,5-dihydro-3-methyl-5-oxo-1H-1,2,4-triazol-1-yl]phenyl]methanesulfonamide to a locus where crabgrass is present.

BACKGROUND OF THE INVENTION

U.S. Pat. No. 3,764,623 discloses Herbicidal Dinitro-1,3-Phenylenediamine Compounds. U.S. Pat. No. 4,818,275 discloses Herbicidal Aryl Triazolinones.

The use of herbicides for crabgrass control in turf is well known. There are two types of herbicide applications for this purpose, pre-emergence herbicides that prevent crabgrass seeds from germinating or emerging and post-emergence herbicides that control emerged and actively growing plants.

Pre-emergence turf herbicides are generally more effective, but must be applied early in the season before crabgrass seeds germinate. In order to provide season-long control most pre-emergent herbicides need to be re-applied six to eight weeks after the initial application. A population of crabgrass, either over an entire site or in localized areas of a site, cannot be confirmed so early in the season, the time and expense of treating turf with pre-emergence applications of herbicides may not be needed.

Post-emergence turf herbicides are used to control crabgrass after germination and emergence from the soil. The benefit of using a post-emergence turf herbicide for crabgrass control is that it is used only if and where crabgrass is present. Some of the most common post-emergence turf herbicides must be reapplied several times, for example, organic arsenicals which include MSMA (monosodium methanearsonate), and DSMA (disodium methanearsonate); and others injure or turn turf grasses yellow after application, for example, fenoxaprop ((+/−)-ethyl 2-[4[(6-chloro-2-benzoxaolyl)oxy]phenoxy}propanoate) and quinclorac(3,7-dichloro-8-quinolinecarboxylic acid).

It would be most beneficial to provide a post-emergence turf herbicide that controlled crabgrass in one application and without injury to turf grasses.

SUMMARY OF THE INVENTION

In accordance with the present invention, it has been found that an herbicidal composition comprising a first herbicide and a second herbicide in which the first herbicide is 2,4-dinitro-$N^3$,$N^3$-dipropyl-6-(trifluoromethyl)-1,3-benzenediamine and the second herbicide is N-[2,4-dichloro-5-[4-(difluoromethyl)-4,5-dihydro-3-methyl-5-oxo-1H-1,2,4-triazol-1-yl]phenyl]methanesulfonamide, wherein the first herbicide and the second herbicide are present in an herbicidal effective amount, has unexpected post-emergence control of crabgrass.

DETAILED DESCRIPTION OF THE INVENTION

It has been unexpectedly found that an herbicidal composition comprising a first herbicide and a second herbicide in which the first herbicide is 2,4-dinitro-$N^3$,$N^3$-dipropyl-6-(trifluoromethyl)-1,3-benzenediamine and the second herbicide is N-[2,4-dichloro-5-[4-(difluoromethyl)-4,5-dihydro-3-methyl-5-oxo-1H-1,2,4-triazol-1-yl]phenyl]methanesulfonamide has advantageous properties in controlling post-emergent crabgrass (*Digitaria* sp.) better than either component alone.

In particular, the present invention is directed to a method for post-emergence crabgrass control by applying a composition comprising a first herbicide and a second herbicide in which the first herbicide is 2,4-dinitro-$N^3$,$N^3$-dipropyl-6-(trifluoromethyl)-1,3-benzenediamine and the second herbicide is N-[2,4-dichloro-5-[4-(difluoromethyl)-4,5-dihydro-3-methyl-5-oxo-1H-1,2,4-triazol-1-yl]phenyl]methanesulfonamide to a locus where one to two leaf growth stage crabgrass is present.

The structural formula of 2,4-dinitro-$N^3$,$N^3$-dipropyl-6-(trifluoromethyl)-1,3-benzenediamine is as follows:

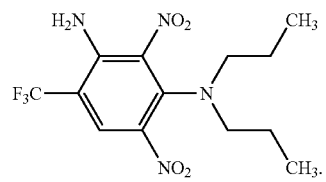

This material, commonly known as prodiamine, is a pre-emergence turf herbicide which can control crabgrass when applied prior to germination and is not effective for post-emergent control.

The structural formula for N-[2,4-dichloro-5-[4-(difluoromethyl)-4,5-dihydro-3-methyl-5-oxo-1H-1,2,4-triazol-1-yl]phenyl]methanesulfonamide is as follows:

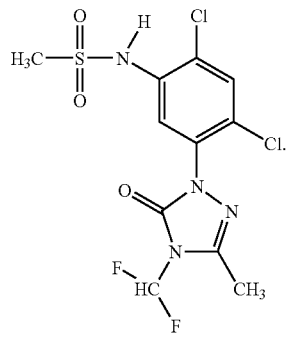 [SMILES: Cc1nn(-c2cc(NS(C)(=O)=O)c(Cl)cc2Cl)c(=O)n1C(F)F]

This material, commonly known as sulfentrazone, is a post-emergence turf herbicide which does not control crabgrass.

The terms "weed" and "weeds" refer to any unwanted vegetation in turf sites. The terms "turf", "turf site" and "turf sites" refers to, but is not limited to, residential and institutional lawns, athletic fields, commercial sod farms and golf course fairways and roughs. The term "ambient temperature" as utilized herein shall generally mean any suitable temperature found in a laboratory or other working quarter, and is generally not below about 15° C. nor above about 30° C. For crabgrass, the one leaf growth stage is herein defined as when a crabgrass leaf first emerges through the soil and is visible. The two leaf growth stage is herein defined as when a crabgrass plant has two visible leaves and a third leaf is not yet visible.

The ratio of 2,4-dinitro-$N^3,N^3$-dipropyl-6-(trifluoromethyl)-1,3-benzenediamine to N-[2,4-dichloro-5-[4-(difluoromethyl)-4,5-dihydro-3-methyl-5-oxo-1H-1,2,4-triazol-1-yl]phenyl]methanesulfonamide varies over a wide range but is usually in the range 10:1 to 1:1, preferably 7:1 to 2:1.

A particular embodiment of the present invention is a method for controlling crabgrass in turf sites which comprises applying a composition of 2,4-dinitro-$N^3,N^3$-dipropyl-6-(trifluoromethyl)-1,3-benzenediamine and N-[2,4-dichloro-5-[4-(difluoromethyl)-4,5-dihydro-3-methyl-5-oxo-1H-1,2,4-triazol-1-yl]phenyl]methanesulfonamide, either together or sequentially, to a locus where crabgrass is present. The herbicidal composition of the present invention is particularly useful in controlling crabgrass in turf sites when applied to the crabgrass plant at the one to two leaf growth stage.

Other herbicides can be employed in conjunction with the first and second herbicides described above providing they do not adversely affect the interaction between the components of this invention. For example it can sometimes be useful to include additional herbicides to extend the range of activity in order to control a wider spectrum of weeds in addition to crabgrass.

The herbicidal compositions of use in the present invention may be employed in many forms and are often most conveniently prepared in aqueous form immediately prior to use. One method of preparing such a composition is referred to as "tank mixing" in which the first and second herbicides in their commercially available forms, either with or without other additives, are mixed together by the user in a quantity of water.

In addition to tank mixing immediately prior to use, the compositions containing 2,4-dinitro-$N^3,N^3$-dipropyl-6-(trifluoromethyl)-1,3-benzenediamine and N-[2,4-dichloro-5-[4-(difluoromethyl)-4,5-dihydro-3-methyl-5-oxo-1H-1,2,4-triazol-1-yl]phenyl]methanesulfonamide may be formulated into a more concentrated primary composition which is diluted with water or other diluent before use. Such compositions may comprise a surface active agent in addition to the active ingredients and examples of such compositions are set forth below.

The herbicidal compounds of use in the present invention can be formulated as a granule of relatively large particle size (for example, 8/16 or 4/8 US Mesh), on fertilizer granules, as water-soluble or water-dispersible granules, as powdery dusts, as wettable powders, as emulsifiable concentrates, as aqueous emulsions, as solutions, or as any of the other known types of agriculturally-useful formulations, depending on the desired mode of application to the areas in which suppression of vegetation is desired. These formulations may contain as little as 0.1%, 0.2% or 0.5% to as much as 95% or more by weight of the total of the two herbicides.

The herbicidal compounds of use in the present invention can be in the form of a dispersible solution which comprises the herbicides dissolved in a water-miscible solvent with the addition of a dispersing agent.

Alternatively, the composition can be in the form of water-soluble or water-dispersible granules that disperse readily in water or other dispersant. Water-soluble or water-dispersible granules normally are prepared to contain about 5-80% of the herbicides, depending on the absorbency of the carrier, and usually also contain a wetting, dispersing or emulsifying agent to facilitate dispersion and may contain a preservative. Typical carriers for water-soluble or water-dispersible granules include Fuller's earth, natural clays, silicas, and other highly absorbent, readily wet inorganic diluents. For example, a useful water-soluble or water-dispersible granule formulation contains 26.71 parts of the herbicidal compounds, 30.90 parts of ammonium sulfate, 30.89 parts of continental clay, 10.00 parts of sodium lignosulfonate as a dispersant, 1.00 part of sodium dioctylsuccinate as a wetting agent and 0.50 part of citric acid as a preservative. The mixture is milled, diluted with water to form a paste and the paste is extruded and dried to produce granules.

Other alternatives that may be employed are dusts which are free flowing admixtures of the herbicides with finely divided solids such as talc, natural clays, kieselguhr, flours such as walnut shell and cottonseed flours, and other organic and inorganic solids which act as dispersants and carriers for the herbicides. These finely divided solids have an average particle size of less than about 50 microns. A typical dust formulation useful herein is one containing 1.0 part or less of the herbicidal compounds and 99.0 parts of talc.

Also useful formulations for the herbicidal compounds of use in the present invention are wettable powders in the form of finely divided particles that disperse readily in water or other dispersant. The wettable powder is ultimately applied to the locus where crabgrass control is needed either as a dry dust or as an emulsion in water or other liquid. Typical carriers for wettable powders include Fuller's earth, kaolin clays, silicas, and other highly absorbent, readily wet inorganic diluents. Wettable powders are prepared to contain about 5-80% of the herbicides, depending on the absorbency of the carrier, and usually also contain a small amount of a wetting, dispersing or emulsifying agent to facilitate dispersion. For example, a useful wettable powder formulation contains 80.0 parts of the herbicidal compounds, 17.9 parts of Palmetto clay, and 1.0 part of sodium lignosulfonate and 0.3 part of sulfonated aliphatic polyester as wetting agents. Additional wetting agents and/or oils will frequently be added to a tank mix to facilitate dispersion on the foliage of the plant.

Other useful formulations for the herbicidal compounds of use in the present invention are emulsifiable concentrates (ECs) which are homogeneous liquid compositions dispersible in water or other dispersant, and may consist entirely of the herbicidal compounds and a liquid or solid emulsifying agent, or may also contain a liquid carrier, such as xylene, heavy aromatic naphthas, isophorone, or other non-volatile organic solvents. For herbicidal application these concentrates are dispersed in water or other liquid carriers and applied as a spray to the area to be treated. The percentage by weight of the herbicidal compounds may vary according to the manner in which the composition is to be applied, but in general comprises 0.5 to 95% of the herbicidal compounds by weight of the total composition.

Flowable formulations may also be employed. These are similar to ECs, except that the herbicidal compounds are suspended in a liquid carrier, generally water. Flowables, like ECs, may include a small amount of a surfactant, and will typically contain the herbicidal compounds in the range of 0.5 to 95%, frequently from 10 to 50%, by weight of the total composition. For herbicidal application, flowables may be diluted in water or other liquid vehicle, and are normally applied as a spray to the area to be treated.

Other useful formulations include suspensions of the herbicidal compounds in a relatively non-volatile solvent such as water, corn oil, kerosene, propylene glycol, or other suitable solvents.

Still other useful formulations for these herbicidal compositions include simple solutions of the herbicides in a solvent in which it is completely soluble at the desired concentration, such as acetone, alkylated naphthalenes, xylene, or other organic solvents. Granular formulations, wherein the herbicides are carried on relative coarse particles, for example, solid fertilizer particles, are of particular utility for aerial distribution, for penetration of cover canopy or for application using a spreader. Pressurized sprays, typically aerosols wherein the herbicides are dispersed in finely divided form as a result of vaporization of a low-boiling dispersant solvent carrier may also be used.

In some circumstances it may be desirable to combine two types of formulations—e.g., one of the herbicidal compounds is used as an emulsifiable concentrate and the other herbicidal compound is dispersed as a powder in this concentrate.

The concentrate of the first and second herbicides (when used as the sole active components) in a composition for direct application to the locus where control is desired by conventional ground methods is preferably within the range of 0.001 to 10% by weight of the composition, especially 0.005 to 5% by weight, but more concentrated compositions containing up to 40% may be desirable.

Typical wetting, dispersing or emulsifying agents that may be used in the compositions of the present invention include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

In use on turf sites, the granular formulations, emulsifiable concentrates, flowable concentrates, aqueous emulsions, solutions, etc., may be diluted with water to give a concentration of the active ingredient in the range of 0.01% or 0.2% to 1.5% or 2.0%.

The application rates of the compositions used in the process of the present invention may vary over a wide range. In general any amount that is effective to control the one to two leaf growth stage crabgrass may be used. Preferred results are achieved at application rates in the range of from about 0.50 to 1.125 lb per acre.

The following examples further illustrate the present invention, but, of course, should not be construed as in any way limiting its scope. The examples include protocols for the evaluation of the compositions of the present invention in which a beneficial effect was observed. The test compositions used were formulated pre-mixes or commercially available formulations of the test compounds. The following commercially available formulations were used: sulfentrazone, Dismiss™ Turf Herbicide from FMC Corporation; prodiamine, Barricade® 4FL Herbicide from Syngenta Crop Protection, Inc.

EXAMPLE 1

Preparation of 2,4-dinitro-$N^3$,$N^3$-dipropyl-6-(trifluoromethyl)-1,3-benzenediamine and N-[2,4-dichloro-5-[4-(difluoromethyl)-4,5-dihydro-3-methyl-5-oxo-1H-1,2,4-triazol-1-yl]phenyl]methanesulfonamide Suspension Concentrate Formulation (SC)

To an appropriately sized mixing vessel, affixed with an overhead mechanical stirrer, was added 749.0 grams of glycerine, 21.2 grams of xanthan gum (Kelzan® M available from Monsanto Chemicals) and 18.7 grams of hydrated magnesium aluminum silicate (Veegum available from R.T. Vanderbuilt Co. Inc.) The mixture was allowed to stir at ambient temperature.

Into an appropriately sized slurry tank was added 4506.0 grams of deionized water, 156.0 grams each of melted Tergitol™ XH and Tergitol™ XD (both of which are alkyl ethylene oxide/propylene oxide copolymers available from Dow Chemical Co.), 280.9 grams of ethoxylated sorbitan monooleate (Agnique SMO-20-U available from Cognis Agrosolutions), 18.7 grams of an isothiazolone mixture (Legend MK preservative, available from Rohm and Haas Corporation) and 12.5 grams of an antifoam agent (Dow Corning AF Emulsion, available from Dow Corning Corporation). The mixture was stirred at ambient temperature for 15 minutes at which time 3,584.8 grams of technical 2,4-dinitro-$N^3$,$N^3$-dipropyl-6-(trifluoromethyl)-1,3-benzenediamine (95.0% active ingredient) was added portion wise followed by 1,852.9 grams of technical N-[2,4-dichloro-5-[4-(difluoromethyl)-4,5-dihydro-3-methyl-5-oxo-1H-1,2,4-triazol-1-yl]phenyl]methanesulfonamide (91.9% active ingredient), also added portion wise. The resultant slurry was milled, in two portions, in an attritor mill until a particle size of less than 11 microns (90% tile) was obtained. The milled slurry was transferred to a second appropriately sized mixing vessel, affixed with an overhead mechanical stirrer. The mill was rinsed with 1127.0 grams of deionized water and the rinsate was added to the second mixing vessel. The glycerin, xanthan gum and hydrated magnesium aluminum silicate mixture prepared above was added to the second mixing vessel and the resultant mixture was stirred at ambient temperature and low shear for two hours. The resultant SC formulation contained 2,4-dinitro-$N^3$,$N^3$-dipropyl-6-(trifluoromethyl)-1,3-benzenediamine and N-[2,4-dichloro-5-[4-(difluoromethyl)-4,5-dihydro-3-methyl-5-oxo-1H-1,2,4-triazol-1-yl]phenyl] methanesulfonamidein a 2:1 ratio and a concentration of 27.28% and 13.64% of the two active ingredients respectively. This SC formulation was packaged into one liter containers for storage.

EXAMPLE 2

Post-emergent herbicidal evaluation of 2,4-dinitro-$N^3$,$N^3$-dipropyl-6-(trifluoromethyl)-1,3-benzenediamine and N-[2,4-dichloro-5-[4-(difluoromethyl)-4,5-dihydro-3-methyl-5-oxo-1H-1,2,4-triazol-1-yl] phenyl]methanesulfonamide on Crabgrass The compositions of the present invention were tested for herbicidal efficacy in the following manner:

For post-emergence testing, three disposable 3 inch square pots for each rate of application of each herbicide solution were filled with a soil, comprised of peat moss, vermiculite, bark ash, pine bark, limestone and a wetting agent (Metro Mix® 360 artificial soil, Scotts Company, Marysville, Ohio), to which about 20 to 30 crabgrass seeds (*Digitaria* sp.) seeds were planted. The pots were placed in a greenhouse and watered daily, thus allowing the seeds to germinate and the foliage to develop for 11 days, until the crabgrass was at the 1-2 leaf growth stage.

Pots designated for treatment were placed on a conveyor belt and the conveyor belt fed under a spray nozzle mounted about ten inches above the postemergent foliage. The spray of herbicidal solution was commenced and once stabilized; the pots were passed under the spray at a speed to receive a coverage equivalent of 30 gallons per acre. The application rates are those shown in Table 1 below for the individual herbicidal solutions and the herbicide compositions of the present invention. The post-emergence pots were immediately placed in the green-house and not watered for 24 hours after treatment. Thereafter they were regularly watered at ground level. The control of crabgrass was evaluated in each experimental test from 1 to 22 days after treatment (DAT). The results, shown as an average of the replications, were compared with results observed in untreated control pots in the same tests. The results are in Table 1 below. All test treatments contained 0.25% (by volume) of a non-ionic surfactant.

Percent control was determined by comparing the treated plants to the untreated control using the following rating system:

Herbicide Rating System

| Rating Percent Control | Description of Main Categories | Weed Description |
|---|---|---|
| 0 | No Effect | No weed control |
| 10 | | Very poor weed control |
| 20 | Slight Effect | Poor weed control |
| 30 | | Poor to deficient weed control |
| 40 | | Deficient weed control |
| 50 | Moderate Effect | Deficient to moderate weed control |
| 60 | | Moderate weed control |
| 70 | | Control somewhat less than satisfactory |
| 80 | Severe | Satisfactory to good weed control |
| 90 | | Very good to excellent weed control |
| 100 | Complete Effect | Complete weed destruction |

The results, shown as an average of the replications, were compared with results observed in untreated control plots in the same trials. The results are in Table 1 below.

TABLE 1

Post-emergence Control of Crabgrass (*Digitaria* sp.) by the Compositions of the Present Invention

| Treatment | Rate of Appln. (lb AI/Acre) | Average % control* Application at the 1-2 Leaf Growth Stage | | | | |
| | | 1 DAT | 3 DAT | 7 DAT | 14 DAT | 22 DAT |
|---|---|---|---|---|---|---|
| A | 0.375 | 10 | 25 | 10 | 0 | 0 |
|   | 0.25 | 20 | 20 | 5 | 0 | 0 |
| B SC | 0.75 ** | 0 | 0 | 0 | 0 | 0 |
| Formulation from Example 1 | 0.75/0.375 | 50 | 60 | 50 | 40 | 50 |
|   | 0.50/0.25 | 40 | 60 | 50 | 40 | 40 |
|   | 0.38/0.19 | 30 | 40 | 10 | 0 | 0 |
| Untreated Control | — | 0 | 0 | 0 | 0 | 0 |

*average of three replications
** Rate of 2,4-dinitro-$N^3$,$N^3$-dipropyl-6-(trifluoromethyl)-1,3-benzenediamine and N-[2,4-dichloro-5-[4-(difluoromethyl)-4,5-dihydro-3-methyl-5-oxo-1H-1,2,4-triazol-1-yl]phenyl]methanesulfonamide, a 2:1 ratio
A = N-[2,4-dichloro-5-[4-(difluoromethyl)-4,5-dihydro-3-methyl-5-oxo-1H-1,2,4-triazol-1-yl]phenyl]methanesulfonamide, Dismiss ™ Turf Herbicide available from FMC Corporation
B = 2,4-dinitro-$N^3$,$N^3$-dipropyl-6-(trifluoromethyl)-1,3-benzenediamine, Barricade ® 4FL Herbicide available from Syngenta Crop Protection, Inc.

Those of ordinary skill in the art will appreciate that variations of the invention may be used and that it is intended that the invention may be practiced otherwise than as specifically described herein. Accordingly, this invention includes all modifications encompassed within the spirit and scope of the invention as defined by the following claims.

What is claimed is:

1. A method for post-emergence crabgrass control said method comprising applying a composition comprising a first herbicide and a second herbicide in which the first herbicide is 2,4-dinitro-$N^3$,$N^3$-dipropyl-6-(trifluoromethyl)-1,3-benzenediamine and the second herbicide is N-[2,4-dichloro-5-[4-(difluoromethyl)-4,5-dihydro-3-methyl-5-oxo-1H-1,2,4-triazol-1-yl]phenyl]methanesulfonamide to a locus where one to two leaf growth stage crabgrass is present.

2. The method of claim 1 wherein the ratio of 2,4-dinitro-$N^3$,$N^3$-dipropyl-6-(trifluoromethyl)-1,3-benzenediamine to N-[2,4-dichloro-5-[4-(difluoromethyl)-4,5-dihydro-3-methyl-5-oxo-1H-1,2,4-triazol-1-yl]phenyl]methanesulfonamide is in the range of from 10:1 to 1:1.

3. The method of claim 2 wherein the ratio of 2,4-dinitro-$N^3$,$N^3$-dipropyl-6-(trifluoromethyl)-1,3-benzenediamine to N-[2,4-dichloro-5-[4-(difluoromethyl)-4,5-dihydro-3-methyl-5-oxo-1H-1,2,4-triazol-1-yl]phenyl]methanesulfonamide is in the range of from 7:1 to 2:1.

4. The method of claim 3 wherein the the ratio is 2:1.

5. The method of claim 4 wherein the application rate is in the range of from 0.50 to 1.125 lb per acre.

\* \* \* \* \*